(12) United States Patent
Powers

(10) Patent No.: US 8,210,024 B2
(45) Date of Patent: Jul. 3, 2012

(54) DAMAGE IMPACTOR

(75) Inventor: Donald E. Powers, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 362 days.

(21) Appl. No.: 12/580,363

(22) Filed: Oct. 16, 2009

(65) Prior Publication Data

US 2011/0088449 A1    Apr. 21, 2011

(51) Int. Cl.
*G01M 7/00* (2006.01)
(52) U.S. Cl. ........................................... 73/12.09
(58) Field of Classification Search ............. 73/12.09
See application file for complete search history.

(56) References Cited

U.S. PATENT DOCUMENTS

| | | | |
|---|---|---|---|
| 3,157,070 A * | 11/1964 | Heidrich | 173/112 |
| 4,682,490 A | 7/1987 | Adelman | |
| 4,967,587 A | 11/1990 | Sirica | |
| 5,048,320 A | 9/1991 | Mitsuhashi | |
| 5,247,835 A | 9/1993 | Howell | |
| 5,823,703 A * | 10/1998 | Thomas et al. | 403/373 |
| 5,983,701 A | 11/1999 | Hassani et al. | |
| 6,941,793 B2 | 9/2005 | Rioux | |

FOREIGN PATENT DOCUMENTS

| | | |
|---|---|---|
| DE | 10009987 | 9/2001 |
| FR | 1517447 | 3/1968 |
| FR | 2323140 | 4/1977 |
| GB | 989944 | 4/1965 |
| JP | 60090037 | 5/1986 |
| WO | WO2008006822 | 1/2008 |

* cited by examiner

*Primary Examiner* — Lisa Caputo
*Assistant Examiner* — Octavia Davis-Hollington
(74) *Attorney, Agent, or Firm* — Caven & Aghevli LLC

(57) ABSTRACT

In one embodiment a damage impactor comprises a housing defining a passage, an impact assembly, an actuator assembly, and an engagement assembly. In one embodiment the impact assembly comprises a guide rod comprising an impact head, and a bias mechanism to bias the guide rod in a first direction. The actuator assembly comprises an actuator, and an actuator rod coupled to the actuator. The engagement assembly selectively couples the impact assembly to the actuator assembly by driving the actuator rod in the first direction to an engagement position where the engagement assembly couples the actuator rod to the guide rod, retracting the actuator rod in a second direction, opposite the first direction, to a release position and releasing the guide rod from the actuator rod. Other embodiments are also disclosed.

23 Claims, 4 Drawing Sheets

DAMAGE IMPACTOR

FIELD OF THE DISCLOSURE

This invention relates to destructive testing, and more particularly to a damage impactor.

BACKGROUND

Various applications require impact damage assessment of one or more components. By way of example, composite materials for use in aircraft require impact testing to demonstrate that the materials remain safe to fly after low velocity/high energy impact damage has occurred. Such impact damage often requires substantial energy levels (i.e., in excess of 2,000 ft-lbs) to be imparted at virtually any angle, on any surface. Thus, apparatus and methods for impact damage testing may find utility.

SUMMARY

In various aspects, apparatus and methods for damage testing are provided. In one aspect there is provided a damage impactor which is comprised of a housing defining a passage, an impact assembly, an actuator assembly, and an engagement assembly. In one embodiment the impact assembly comprises a guide rod comprising an impact head, and a bias mechanism to bias the guide rod in a first direction. The actuator assembly comprises an actuator, and an actuator rod coupled to the actuator. The engagement assembly selectively couples the impact assembly to the actuator assembly by driving the actuator rod in the first direction to an engagement position where the engagement assembly couples the actuator rod to the guide rod, retracting the actuator rod in a second direction, opposite the first direction, to a release position; and releasing the guide rod from the actuator rod.

In another aspect there is provided an engagement assembly to couple a first moveable shaft to a second moveable shaft. In one embodiment, the engagement assembly comprises a plurality of lift jaw members pivotably mounted to a distal end of the first shaft, and pivotable between a first position in which the lift jaw members engage a lift ring on the second shaft and a second position in which the lift jaw members disengage from a lift ring on the second shaft, a clamp ring to retain the lift jaw members into the first position, and a release ring to disengage the lift jaw members from the clamp ring.

In yet another aspect there is provided a method to apply an impact damage to a surface. In one embodiment the method comprises positioning a damage impactor proximate to a surface. In one embodiment the damage impactor comprises a housing defining a passage, an impact assembly comprising a guide rod comprising an impact head, a bias mechanism to bias the guide rod in a first direction, an actuator assembly, comprising an actuator, an actuator rod coupled to the actuator, and an engagement assembly to selectively couple the impact assembly to the actuator assembly. The method further comprises activating the actuator assembly to drive the actuator rod in the first direction to an engagement position where the engagement assembly couples the actuator rod to the guide rod to retract the actuator rod in a second direction, opposite the first direction, to a release position, and release the guide rod from the actuator rod.

The features, functions and advantages discussed herein can be achieved independently in various embodiments described herein or may be combined in yet other embodiments, further details of which can be seen with reference to the following description and drawings.

BRIEF DESCRIPTION OF THE DRAWINGS

The detailed description is described with reference to the accompanying figures.

DETAILED DESCRIPTION

Described herein are exemplary apparatus and methods for impact damage testing. In the following description, numerous specific details are set forth to provide a thorough understanding of various embodiments. However, it will be understood by those skilled in the art that the various embodiments may be practiced without the specific details. In other instances, well-known methods, procedures, components, and circuits have not been illustrated or described in detail so as not to obscure the particular embodiments.

Figure 1:
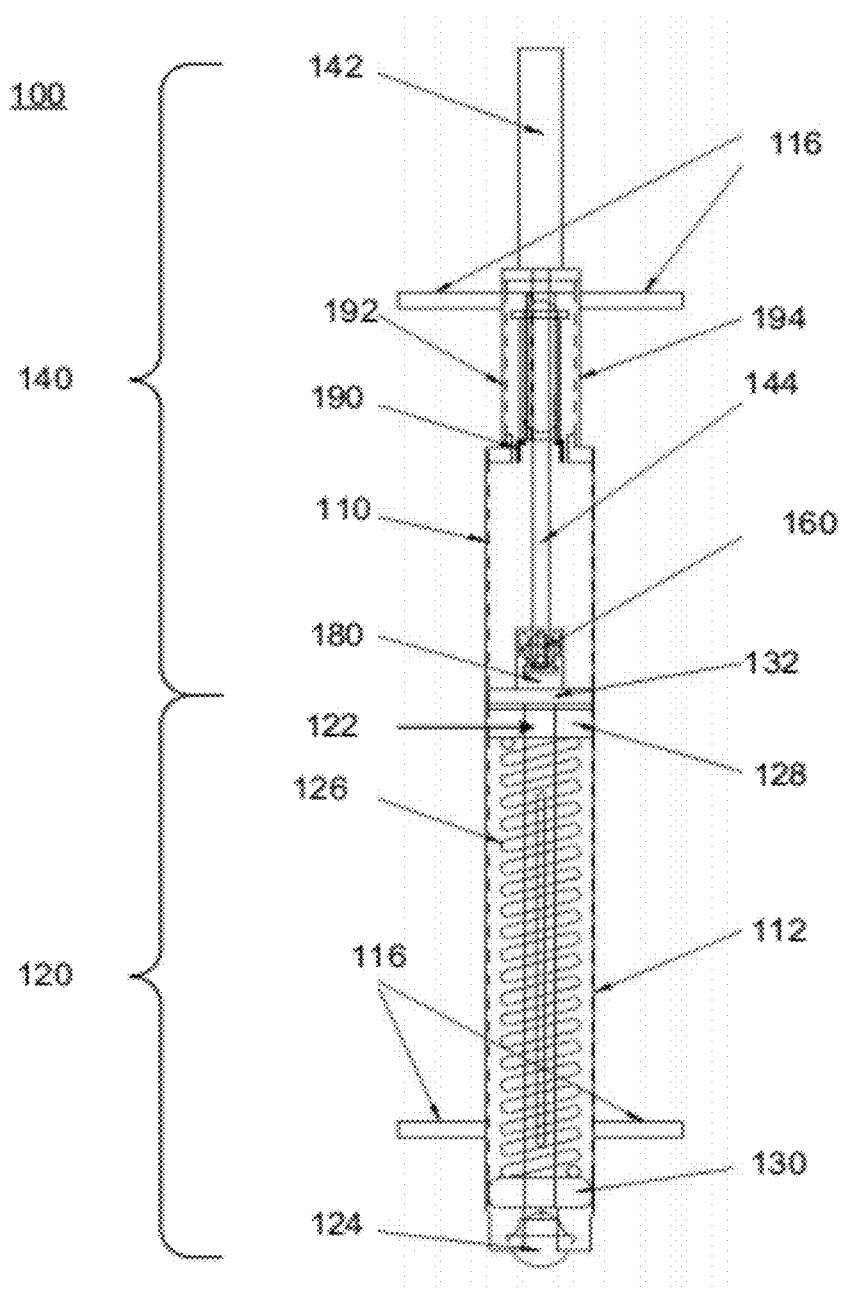
FIG. 1 is a schematic illustration of a damage impactor in accordance with some embodiments.
Figure 2:
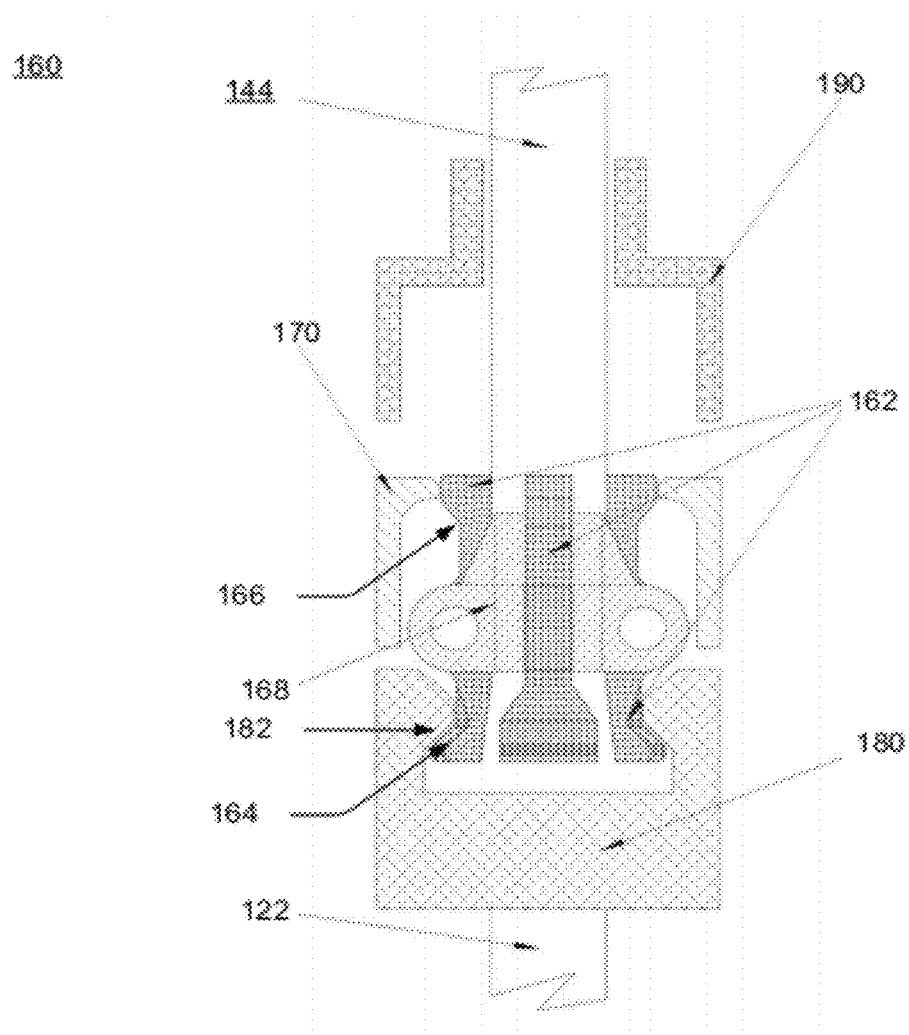
FIG. 2 is a schematic illustration of an engagement assembly for a damage impactor, according to embodiments.
Figure 3:
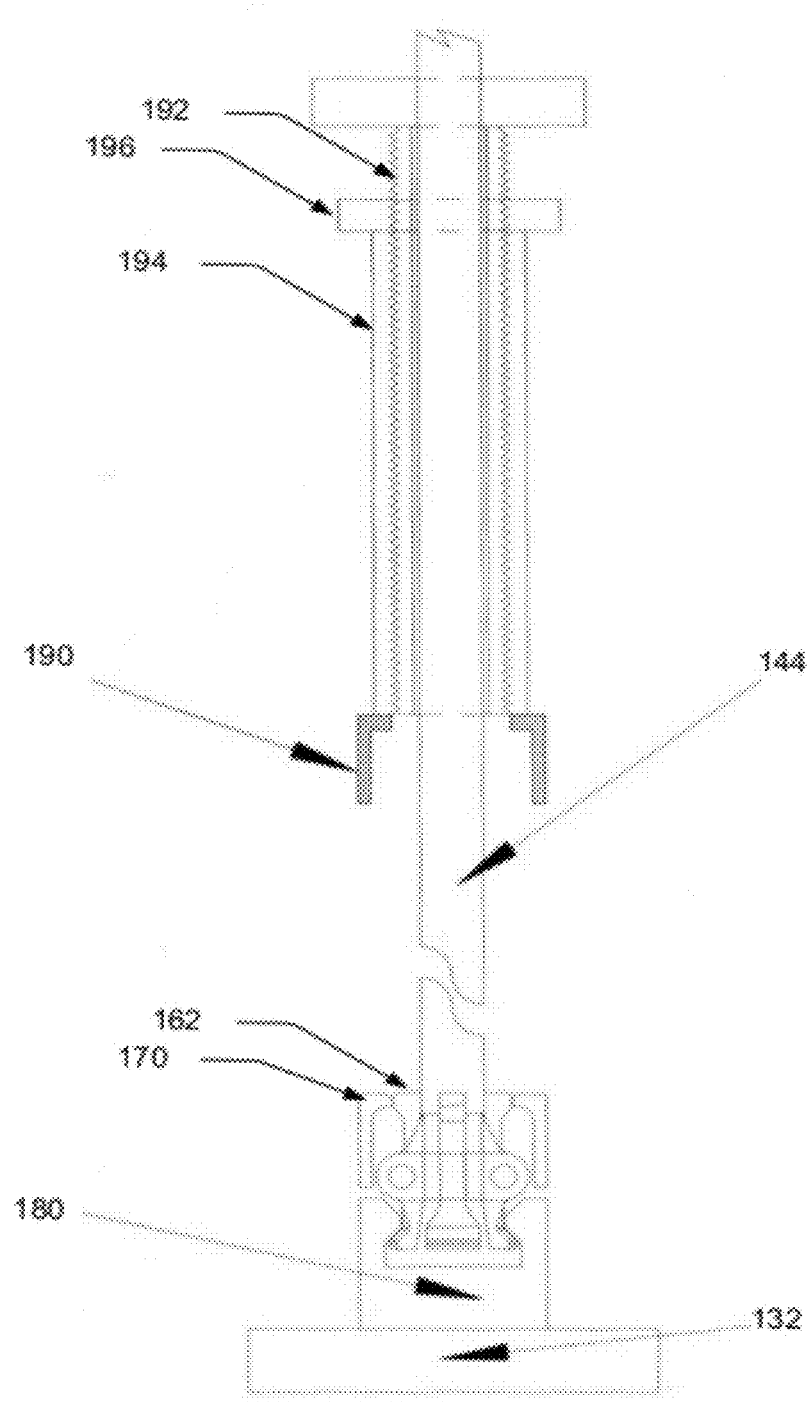
FIG. 3 is a schematic illustration of an engagement assembly for a damage impactor, according to embodiments.

Referring to FIGS. 1-3, one embodiment of a damage impactor will be described. Referring first to FIG. 1, a damage impactor 100 is depicted. In the embodiment depicted in FIG. 1, the damage impactor comprises a housing 110, an impact assembly 120, an actuator assembly 140, and an engagement assembly 160 to selectively couple the impact assembly 120 to the actuator assembly 140. In one embodiment the housing 110 comprises a plurality of support arms 116 mounted to the housing 110.

In the embodiment depicted in FIGS. 1-3, the impact assembly 120 comprises a guide rod 122 comprising an impact head 124 mounted on a distal end of the guide rod 122, and a bias mechanism 126 to bias the guide rod in a first direction, i.e., in a direction toward the impact head 124. In the embodiment depicted in FIG. 1, the bias mechanism 126 comprises a compression spring which biases the impact assembly in the first direction. The compression spring is compressed between a first reaction plate 128 and a second reaction plate 130. The first reaction plate 128 remains in a substantially fixed position in the housing 110. The second reaction plate 130 is attached to a distal end of guide rod 122, between the end of guide rod 122 and impact head 124, all of which are moveable within the housing 110. The interior surface of the housing 110 comprises a plurality of guides 112 which guide second reaction plate 130 in position as it moves within the housing 110. In one embodiment the guides 112 comprise narrow strips running axially on the interior of the housing 110 which are formed from a material which facilitates the movement of the second reaction plate 130 within the housing, e.g., Teflon®, or the like.

The impactor assembly 120 further comprises a stroke limit plate 132 which is fixedly mounted to the proximal end of guide rod 122 opposite of the impact head and which serves to limit the stroke length of the impact assembly. In some embodiments the compression spring 126 has a spring constant that measures between 250 Lbf/inch and 750 Lbf/inch, and preferably about 500 Lbf/inch. The various spring constants allow different ranges of impact energies to be achieved with the same apparatus and with better accuracy.

The actuator assembly 140 extends and retracts the actuator rod 144 within the housing 110. In the embodiment depicted in FIG. 1, the actuator assembly 140 comprises an actuator 142 and an actuator rod 144 coupled to the actuator 142. The actuator may be implemented as one or more of a hydraulic actuator, a pneumatic actuator, an electromagnetic actuator, or the like. The particular implementation of the actuator will be a function of design parameters, e.g., the amount of force required to retract the compression spring 126 to achieve a desired energy level. In the embodiment depicted in FIG. 1, the actuator 142 may be embodied as a hydraulic actuator.

The engagement assembly 160 operates to selectively couple the impact assembly 120 to the actuator assembly 140. Referring to FIGS. 1-3, the engagement assembly 160 comprises a plurality of lift jaw members 162 pivotably mounted to a pivot block 168 on the distal end of the actuator rod 144, and pivotable between a first position in which the lift jaw members 162 engage a lift ring 180 on the guide rod 122 and a second position in which the lift jaw members 162 disengage from a lift ring 180 on the guide rod 122. In the depicted embodiment, the plurality of lift jaw members 162 comprise a key-shaped lower outer surface 164. Similarly, the lift ring 180 comprises a key-shaped inner surface 182, such that when the lift jaw 162 engages the lift ring, the key-shaped outer surface of the lift jaw members 162 engages with the key-shaped inner surface 182 of the lift ring 180.

The engagement assembly 160 further comprises a clamp ring 170 to retain the lift jaw members 162 into the first position, and a release ring 190 to disengage the lift jaw members 162 from the clamp ring 170. As best illustrated in FIG. 2, the plurality of lift jaw members 162 further comprise a key-shaped upper outer surface 166 such that the clamp ring 170 engages the key-shaped upper surface 166 with a friction fit, when the actuator rod 144 is fully extended to the engagement position, thereby locking the lift jaw members 166 to the lift ring 180.

The release ring 190 functions to block motion of the clamp ring 170 as the actuator rod 144 is retracted, such that the jaw members 162 are disengaged from the lift jaw 180. As illustrated in FIG. 3, in one embodiment the position of the release ring 190 is adjustable, such that the retraction stroke length of the impactor assembly is variable. In the embodiment depicted in FIG. 3, the clamp ring 190 is disposed on a mount 194 that is mounted on threads 192 on the housing, such that the position of clamp ring 190 can be adjusted by rotating the mount 194 with respect to the threads. A top plate 196 provides the means to physically adjust the position of release ring 190. In this embodiment the outer circumference of the top plate 196 is knurled to improve the ability to spin the threaded mount 194.

The particular materials from which the damage impactor 100 are formed are not critical and are primarily a function of design necessity to support the forces generated by the compression spring 126. In one embodiment the various components of the damage impactor 100 are formed from steel or another suitable metal.

Similarly, the particular size of the impactor 100 and its components is not critical. The dimensions of the impactor are primarily a function of design necessity in order to encompass the apparatus to afford functionality and safety considerations. In one embodiment the damage impactor 100 measures approximately 75 inches in height, and 6 inches in diameter, and supports a stroke length of between 3 inches and 12 inches, such that the impactor can deliver an impact force between 800 foot-pounds and 2000 foot-pounds via the impact head 124.

Figure 4:
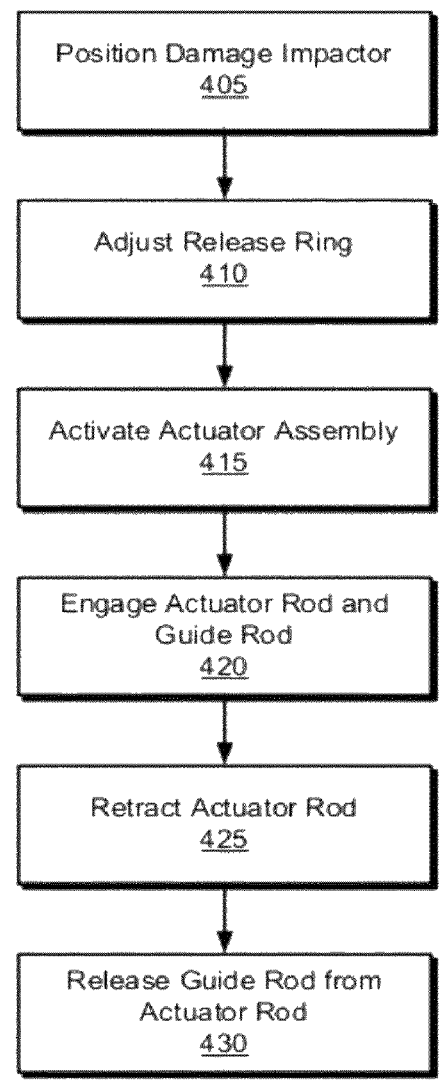
FIG. 4 is a flowchart illustrating operations in a method to use a damage impactor, according to embodiments.

Having described features of the damage impactor, operation of the damage impactor will now be described with reference to FIG. 4, which is a flowchart illustrating operations in a method to use a damage impactor, according to embodiments. Referring to FIG. 4, at operation 405 the damage impactor 100 is positioned proximate the surface to be tested such that the impact head is in contact with the surface before the actuator assembly retracts the actuator rod. The damage impactor 100 may be positioned at any angle with respect to the surface, and at any angle with respect to the Earth. The damage impactor 100 may be secured in place by rigging the support arms 116 to external support members.

At operation 410 the position of the release ring may be adjusted to adjust the force on the compression spring. As described above, this adjustment may be accomplished by rotating the mount 194 with respect to the threads 192 on the housing.

At operation 415 the actuator assembly 140 is activated. As described above, the actuator 142 may be a hydraulic actuator. Activating the actuator assembly drives the actuator rod 144 in a first direction toward the distal end of the damage impactor 100 to an engagement position where the engagement assembly 160 engages (operation 420) the actuator rod 144 and the guide rod 122. As the engagement assembly reaches the engagement position the plurality of lift jaw members 162 are forced into position to engage the lift ring on the impactor guide rod 122 by engaging the clamping ring 170 with the upper surface 166 of the lift jaws. As the actuator rod 144 continues to extend in the distal direction, the clamping ring 170 is forcefully driven onto the top surfaces of the lift jaw members 166, creating a friction fit locking the clamping ring 170 onto the upper surface of the lift jaw members 166.

The actuator rod 144 is then retracted (operation 420) in a second direction, opposite the first direction. As the actuator rod 144 retracts the upper surface 166 of the lift jaw members 162 engages the lower surface 182 of the lift ring, such that the lower surface 164 of the lift jaw members 162 is engaged with the surface 182 of the lift ring 180.

Retracting the actuator rod 144 and the guide rod 122 compresses the spring 126, thereby loading the damage impactor with a spring force. Continued retraction causes the clamp ring 170 to contact the release ring 190. The clamp ring 170 is moveable relative to the actuator rod 144. The release ring 190 limits the motion of the clamp ring 170, thereby allowing the actuator rod 144 and the attached lift jaw members 162 to break free from the clamp ring 170. This, in turn, allows the lift jaw members 162 to pivot on the pivot block 168 such that the lift block 180 is released from the lift jaw members 162, thereby disengaging the actuator rod 144 from the guide rod 122. At this point the energy stored in the compression spring 126 is released, and the compression spring 126 drives the guide rod 122 and the impact head 124 toward the surface of the object being tested. The operations depicted in FIG. 4 may be repeated in order to implement multiple impact tests of the surface.

Reference in the specification to "one embodiment" or "some embodiments" means that a particular feature, structure, or characteristic described in connection with the embodiment is included in at least an implementation. The appearances of the phrase "in one embodiment" in various places in the specification may or may not be all referring to the same embodiment.

Although embodiments have been described in language specific to structural features and/or methodological acts, it is to be understood that claimed subject matter may not be limited to the specific features or acts described. Rather, the specific features and acts are disclosed as sample forms of implementing the claimed subject matter.

What is claimed is:

1. A damage impactor, comprising:
a housing defining a passage;
an impact assembly, comprising:
a guide rod comprising an impact head;
a bias mechanism comprising a compression spring to bias the guide rod in a first direction;
a first reaction plate and a second reaction plate; and
a stroke limit plate
an actuator assembly, comprising:
an actuator;
an actuator rod coupled to the actuator; and
an engagement assembly to selectively couple the impact assembly to the actuator assembly,
wherein the actuator assembly:
drives the actuator rod in the first direction to an engagement position at which the engagement assembly couples the actuator rod to the guide rod;
retracts the actuator rod in a second direction, opposite the first direction, to a release position; and
releases the guide rod from the actuator rod.

2. The damage impactor of claim 1, wherein the housing comprises:
one or more guides disposed within in the body.

3. The damage impactor of claim 1, wherein the engagement assembly comprises:
a plurality of lift jaw members pivotably mounted to a distal end of the actuator rod, and pivotable between a first position in which the lift jaw members engage a lift ring on the guide rod and a second position in which the lift jaw members disengage from a lift ring on the guide rod;
a clamp ring to retain the lift jaw members into the first position; and
a release ring to disengage the lift jaw members from the clamp ring.

4. The damage impactor of claim 3, wherein:
the plurality of lift jaw members comprise a key-shaped lower outer surface; and
the lift ring comprises a key-shaped inner surface, such that the when the lift jaw engages the lift ring, the key-shaped outer surface of the lift jaw members engages with the key-shaped inner surface of the lift ring.

5. The damage impactor of claim 4, wherein:
the plurality of lift jaw members further comprise a key-shaped upper outer surface; and
the clamp ring engages the key-shaped upper surface when the actuator rod is retracted from the engagement position, thereby locking the lift jaw members to the lift ring.

6. The damage impactor of claim 5, wherein the release ring blocks motion of the clamp ring as the actuator rod is retracted, such that the jaw members are disengaged from the lift jaw.

7. The damage impactor of claim 6, wherein the position of the release ring relative to the distal end of the actuator rod is adjustable.

8. The damage impactor of claim 7, further comprising a plurality of support arms mounted to the housing.

9. An engagement assembly to couple a first moveable shaft to a second moveable shaft, comprising:
a plurality of lift jaw members pivotably mounted to a distal end of the first shaft, and pivotable between a first position in which the lift jaw members engage a lift ring on the second shaft and a second position in which the lift jaw members disengage from a lift ring on the second shaft;
a clamp ring to retain the lift jaw members into the first position; and
a release ring to disengage the lift jaw members from the clamp ring,
wherein:
the plurality of lift jaw members comprise a key-shaped lower outer surface; and
the lift ring comprises a key-shaped inner surface, such that the when the lift jaw engages the lift ring, the key-shaped outer surface of the lift jaw members engages with the key-shaped inner surface of the lift ring.

10. The engagement assembly of claim 9, wherein:
the plurality of lift jaw members further comprise a key-shaped upper outer surface; and
the clamp rings engage the key-shaped upper surface when the first shaft is retracted from the engagement position, thereby locking the lift jaw members to the lift ring.

11. The engagement assembly of claim 10, wherein the release ring blocks motion of the clamp rings as the first shaft is retracted, such that the clamp ring is disengaged from the lift jaw.

12. The engagement assembly of claim 11, wherein the position of the release ring relative to the distal end of the first shaft.

13. A method to apply an impact damage to a surface, comprising:
positioning a damage impactor proximate the surface, the damage impactor comprising:
a housing defining a passage;
an impact assembly, comprising:
a guide rod comprising an impact head;
a bias mechanism to bias the guide rod in a first direction;
an actuator assembly, comprising:
an actuator;
an actuator rod coupled to the actuator; and
an engagement assembly to selectively couple the impact assembly to the actuator assembly, wherein the engagement assembly comprises:
a plurality of lift jaw members pivotably mounted to a distal end of the actuator rod, and pivotable between a first position in which the lift jaw members engage a lift ring on the impactor guide rod and a second position in which the lift jaw members disengage from a lift ring on the impactor guide rod;
a clamp ring to retain the lift jaw members into the first position; and
a release ring to disengage the lift jaw members from the clamp ring; and
activating the actuator assembly to:
drive the actuator rod in the first direction to an engagement position where the engagement assembly couples the actuator rod to the guide rod;
retract the actuator rod in a second direction, opposite the first direction, to a release position; and
release the guide rod from the actuator rod.

14. The method of claim 13, wherein positioning the damage impactor proximate the surface comprises positioning the damage impactor such that the impact head is in contact with the surface before the actuator assembly retracts the actuator rod.

15. The method of claim 13, wherein:
the plurality of lift jaw members comprise a key-shaped lower outer surface; and
the lift ring comprises a key-shaped inner surface, such that the when the lift jaw engages the lift ring, the key-shaped outer surface of the lift jaw members engages with the key-shaped inner surface of the lift ring.

16. The method of claim 15, wherein:
the plurality of lift jaw members further comprise a key-shaped upper outer surface; and
the clamp rings engage the key-shaped upper surface when the actuator rod is retracted from the engagement position, thereby locking the lift jaw members to the lift ring.

17. A damage impactor, comprising:
a housing defining a passage;
an impact assembly, comprising:
 a guide rod comprising an impact head;
 a bias mechanism to bias the guide rod in a first direction;
an actuator assembly, comprising:
 an actuator;
 an actuator rod coupled to the actuator; and
an engagement assembly to selectively couple the impact assembly to the actuator assembly, wherein the engagement assembly comprises:
 a plurality of lift jaw members pivotably mounted to a distal end of the actuator rod, and pivotable between a first position in which the lift jaw members engage a lift ring on the guide rod and a second position in which the lift jaw members disengage from a lift ring on the guide rod;
 a clamp ring to retain the lift jaw members into the first position; and
 a release ring to disengage the lift jaw members from the clamp ring,
wherein the actuator assembly:
 drives the actuator rod in the first direction to an engagement position at which the engagement assembly couples the actuator rod to the guide rod;
 retracts the actuator rod in a second direction, opposite the first direction, to a release position; and
releases the guide rod from the actuator rod.

18. The damage impactor of claim 17, wherein the housing comprises:
one or more guides disposed within in the body.

19. The damage impactor of claim 17, wherein the bias mechanism comprises a compression spring which biases the impact assembly in the first direction.

20. The damage impactor of claim 19, wherein the impact assembly comprises:
a first reaction plate and a second reaction plate; and
a stroke limit plate.

21. The damage impactor of claim 17, wherein:
the plurality of lift jaw members comprise a key-shaped lower outer surface; and
the lift ring comprises a key-shaped inner surface, such that the when the lift jaw engages the lift ring, the key-shaped outer surface of the lift jaw members engages with the key-shaped inner surface of the lift ring.

22. The damage impactor of claim 21, wherein:
the plurality of lift jaw members further comprise a key-shaped upper outer surface; and
the clamp ring engages the key-shaped upper surface when the actuator rod is retracted from the engagement position, thereby locking the lift jaw members to the lift ring.

23. The damage impactor of claim 22, wherein the release ring blocks motion of the clamp ring as the actuator rod is retracted, such that the jaw members are disengaged from the lift jaw.

* * * * *